(12) United States Patent
Jeng

(10) Patent No.: US 6,499,495 B2
(45) Date of Patent: Dec. 31, 2002

(54) WASTE TREATMENT SYSTEM FOR SUCTION CANISTERS

(75) Inventor: David K. Jeng, Lisle, IL (US)

(73) Assignee: Allegiance Corporation, McGaw Park, IL (US)

( * ) Notice: Subject to any disclaimer, the term of this patent is extended or adjusted under 35 U.S.C. 154(b) by 180 days.

(21) Appl. No.: 09/769,934

(22) Filed: Jan. 24, 2001

(65) Prior Publication Data

US 2002/0096193 A1 Jul. 25, 2002

(51) Int. Cl.[7] ................................................. B08B 9/08
(52) U.S. Cl. ........................ 134/169 R; 134/58 R; 134/62; 134/95.1; 134/170; 134/22.18; 422/292; 422/299
(58) Field of Search ............................... 134/62, 169 R, 134/58 R, 18, 22.18, 26, 95.1, 170, 16; 422/27, 299, 300, 28, 292

(56) References Cited

U.S. PATENT DOCUMENTS

| 3,916,924 | A | | 11/1975 | McGowan | 134/95 |
| 4,058,412 | A | | 11/1977 | Knapp et al. | 134/24 |
| 4,653,518 | A | * | 3/1987 | Adachi | 134/144 |
| 4,695,385 | A | | 9/1987 | Boag | 210/636 |
| 4,731,222 | A | | 3/1988 | Kralovic et al. | 422/37 |
| 4,961,440 | A | | 10/1990 | Wright | 134/167 |
| 4,967,776 | A | * | 11/1990 | Folmar | 134/103.1 |
| 5,087,420 | A | | 2/1992 | Jackson | 422/37 |
| 5,449,009 | A | * | 9/1995 | Kerwin et al. | 134/103.1 |
| 5,458,851 | A | | 10/1995 | Schroeder et al. | 422/28 |
| 5,545,802 | A | | 8/1996 | Narbonne | 588/249 |
| 5,589,145 | A | * | 12/1996 | Kaufman | 206/438 |
| 5,637,103 | A | * | 6/1997 | Kerwin et al. | 134/150 |
| 5,723,095 | A | | 3/1998 | Fricker et al. | 422/292 |
| 5,736,098 | A | * | 4/1998 | Kerwin et al. | 134/26 |
| 5,741,237 | A | * | 4/1998 | Walker | 134/50 |
| 5,776,260 | A | | 7/1998 | Dunn et al. | 134/18 |
| 5,807,359 | A | | 9/1998 | Bemis et al. | 604/322 |
| 5,914,047 | A | * | 6/1999 | Griffiths | 210/101 |
| 5,945,004 | A | * | 8/1999 | Ohira et al. | 210/202 |
| 6,263,887 | B1 | * | 7/2001 | Dunn | 134/140 |

* cited by examiner

Primary Examiner—Alexander Markoff
(74) Attorney, Agent, or Firm—Donald O. Nickey; Andrew G. Rozycki

(57) ABSTRACT

The present invention provides an apparatus and method for treatment of waste from suction canisters. The waste treatment system includes a canister-cleaning and a reservoir chamber. The canister-cleaning chamber holds the suction canister to be treated. The reservoir chamber is fluidly connected to the canister-cleaning chamber and to a water source. The reservoir chamber adapted to be raised and lowered relative to the canister-cleaning chamber to permit cleaning fluids to flow to and from the canister cleaning-chamber.

8 Claims, 6 Drawing Sheets

WASTE TREATMENT SYSTEM FOR SUCTION CANISTERS

FIELD OF THE INVENTION

The present invention relates to a waste treatment system for suction canisters which sanitizes used suction canisters for "white bag" disposal while minimizing exposure of health care personnel to potentially harmful microbes.

BACKGROUND OF THE INVENTION

Medical suction canisters are used to drain bodily fluids from a patient, especially during various surgical procedures. Typically, the body fluid collected in the suction canisters is disposed directly into a sewage system by hospital personnel. However, the splatter and aerosol often created during the disposal process creates a risk that hospital personnel may be exposed to potentially dangerous infective agents such as for example, HIV, Hepatitis B or tuberculosis. In addition, many of the conventional suction canisters used are disposable, single use canisters. Due to the potentially contagious nature of the fluids collected in the suction canisters, the suction canisters are disposed of in "red bags." Red bag disposal requires disinfective treatment before disposal and is relatively more expensive than "white bag" disposal (no disinfection required) which leads to increased costs.

Prior art devices and methods have attempted to minimize hospital personnel exposure to potentially contagious agents during the draining of suction canisters. U.S. Pat. No. 5,545,802 discloses a method that involves the introduction of an antimicrobial into the fluid while it is still within the suction canister to reduce the infectious nature of the contained waste thereby minimizing exposure to dangerous microbes. However, to effectively disinfect the suction canister, it is necessary for the antimicrobial to physically contact the microbes and to cover the entire interior wall of the suction canister. Otherwise, it is possible that the potentially hazardous microbes will survive and re-grow.

U.S. Pat. No. 5,087,420 discloses a method that involves the introduction of a solidifier into the suction canister to convert the body fluids into a semi-solid gel to minimize splatter and aerosol. The solidifier typically includes an antiseptic additive. However, the addition of the solidifier further reduces the chances that the antiseptic additive will cover the entire interior wall of the suction canister.

One prior art device involves the cleaning and disinfecting of reusable suction canisters. Suction canisters containing the body fluids are placed in a sealed chamber. Antiseptics are added and water jets are employed to mix the body fluids with the antiseptics. The disinfected contents of the suction canister are drained and the suction canister is ready for reuse. However, the reusable canisters are designed with cumbersome moving parts which may disengage from the canisters and potentially disrupt the cleaning cycle. In addition, the manufacture of the specially designed suction canisters is costly. Further, not only may the aerosol created by the water jets pose a health concern, but also potential risks associated with the reuse of suction canisters may create additional liability issues.

Another method utilizes an automated centralized waste treatment system. A filled suction canister is placed within a sealed chamber and tubing connected to a vacuum source is inserted into the interior of the suction canister. The contents of the suction canister are essentially vacuumed out of the canister to a sewage drain for disposal. The emptied suction canister is then discarded in a red bag. Not only is this prior art system very expensive to purchase, the suction canisters are disposed in a red bag as opposed to in a less costly white bag.

U.S. Pat. No. 4,058,412 relates to a device for washing a can that utilizes a support for supporting the can on one of its lateral sides for sliding movement from a pre-punch position to a punch position. A knife is used to pierce the bottom of the can and a spray nozzle is mounted with respect to the knife so as to protrude within the interior of the can whenever the knife pierces the can.

U.S. Pat. No. 5,776,260 discloses a liquid waste disposal and canister flushing system. The flushing system includes a cabinet with a sink for receiving the canister and a sub-sink for receiving a lowered portion thereof. The sub-sink is connected to a drain line. A plunger subassembly includes a stopper which functions as a drain valve for the canister. An injection jet is connected to water and cleaning solution and discharges diluted cleaning solution into the canister for flushing same. A control system includes a programmable microprocessor which can be programmed to provide drain and flush cycles of predetermined duration.

U.S. Pat. No. 4,961,440 discloses an apparatus for emptying and rinsing containers of chemicals. The apparatus includes a chamber in which the container can be enclosed and supported, draining means and a hollow, perforated wash pipe. The chamber is provided with means for supporting the container in a generally tilted manner such that a corner thereof is presented as the lowest portion and the wash pipe is arranged to pierce the container through said corner.

None of the prior art suggests or discloses a waste treatment system for suction canisters that includes a canister cleaning chamber for holding the suction canister to be treated, a reservoir chamber fluidly connected to the canister cleaning chamber and to a source of water, the reservoir chamber adapted to be raised and lowered relative to the canister cleaning chamber so as to permit cleaning fluids to flow to and from the canister cleaning chamber.

Thus what is needed is a device for disposing of body fluids contained within suction canisters while minimizing the exposure of hospital personnel to potentially harmful microbes. The system and method of the present invention fulfills these needs and treats treat body fluids so that they can be safely discarded in a public sewage system. The present invention will also sanitize disposable suction canisters so that they can be disposed of in less expensive white bags. The device according t the invention also has a fairly simple design so that it has relatively low manufacturing costs.

SUMMARY OF THE INVENTION

The present invention provides for the disposal of body fluids contained within suction canisters while minimizing the exposure of hospital personnel to potentially harmful microbes. The present invention further treats the body fluids so that they can be safely discarded in a public sewage system and sanitizes disposable suction canisters so that they can be disposed of in the less expensive "white bags". The present invention provides these advantages at a relatively low manufacturing cost.

The present invention provides a waste treatment system for suction canisters. The waste treatment system includes a connection to a sewage system, a canister-cleaning chamber and a reservoir chamber. The canister-cleaning chamber holds the suction canister to be treated. The reservoir chamber is fluidly connected to the canister-cleaning chamber, to the canister-disinfecting chamber, and to a water source. The reservoir chamber is adapted to be raised and lowered relative to the canister-cleaning chamber to permit the disinfectant and cleaning fluids to flow into and out of the canister cleaning-chamber.

Thus, there is disclosed a waste treatment system for suction canisters comprising a canister-cleaning chamber for holding the suction canister to be treated and a reservoir chamber fluidly connected to the canister cleaning chamber and to a water source. The reservoir chamber is adapted to be raised and lowered relative to the canister-cleaning chamber to permit cleaning fluids to flow into and out of the canister-cleaning chamber.

There is also disclosed a method of treating waste comprising the steps of placing a suction canister into a canister-cleaning chamber through an opening; closing the opening to create a sealed canister-cleaning chamber; channeling water from a water source to the reservoir chamber and opening a drainage on the suction canister thereby permitting the body fluids to drain out of the suction canister into the reservoir chamber.

There is further disclosed a method of treating waste comprising the steps of lowering a reservoir chamber to the canister-cleaning chamber; placing a suction canister containing body fluids within the canister-cleaning chamber; releasing a volume of water from a water source into the reservoir chamber and creating a drainage opening in the suction canister thereby draining the waste out of the suction canister into the reservoir chamber.

Another embodiment of the method of the present invention includes placing a suction canister into a canister-cleaning chamber through an opening; closing the opening to create a sealed canister-cleaning chamber; channeling water from a water source to the reservoir chamber; and opening a drainage on the suction canister by pivoting downward on a hand bar to break a release port disposed on the suction canister thereby permitting the body fluids to drain out of the suction canister into the reservoir chamber.

Lastly, the present invention relates to a cabinet for housing a waste treatment system for suction canisters comprising a reload door providing access to a disinfectant source with plumbing connected from a source of water to said water treatment system. A sliding door will provide access to a canister-cleaning chamber for loading and unloading the suction canister and a drain is provided to dispose of water from the water treatment system. This cabinet is controlled by a control panel which has a power switch, a first indicator light, a second indicator light and an operating switch.

DETAILED DESCRIPTION OF THE PREFERRED EMBODIMENTS

Figure 1:
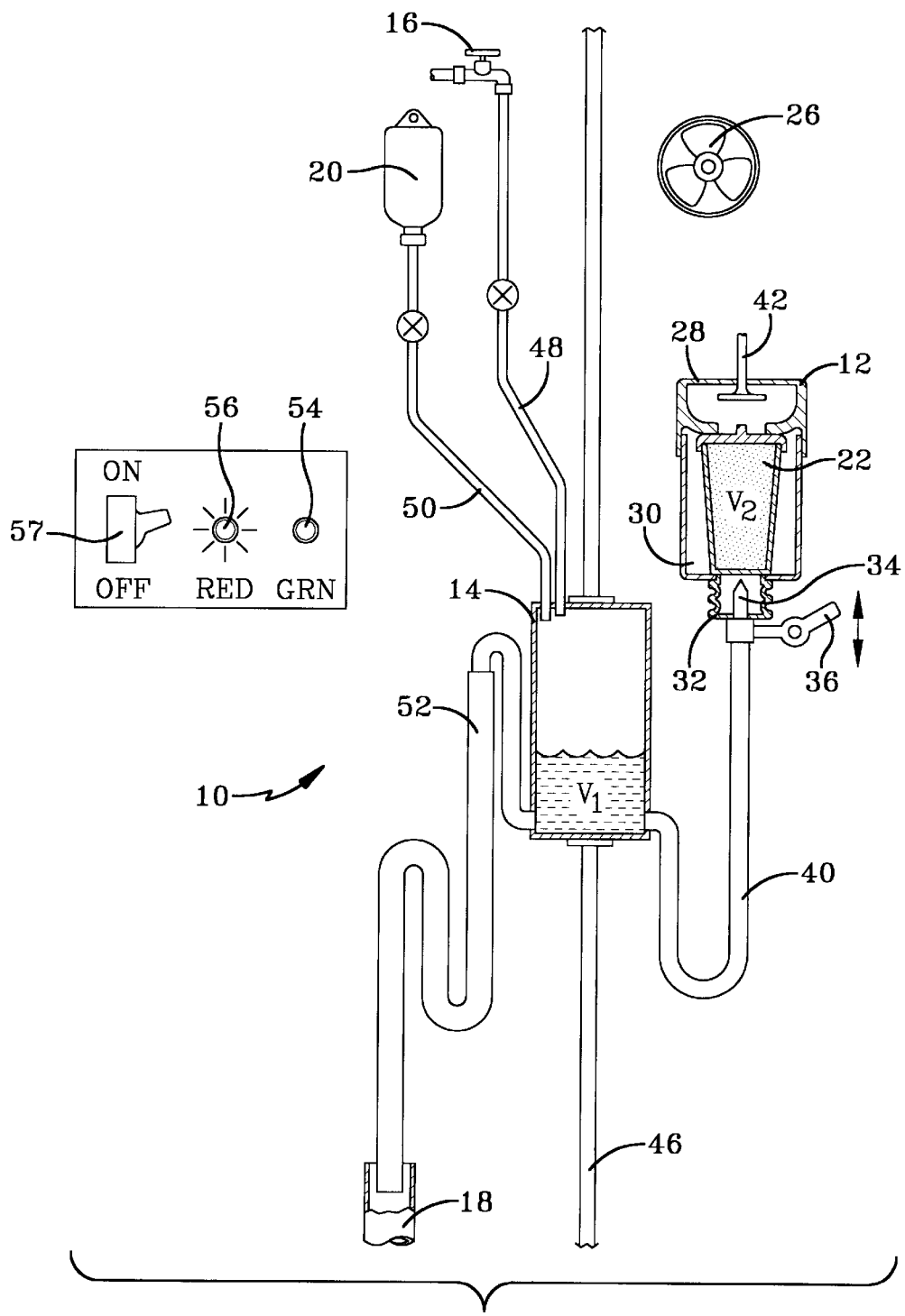
FIG. 1 is a front view in partial cross section of a preferred embodiment of a waste treatment system for suction canisters in accordance with the principles of the present invention.

Referring now to FIG. 1, a preferred embodiment of a waste treatment system for suction canisters in accordance with the principles of the present invention is generally designated as 10. The waste treatment system 10 is generally designed to sanitize and drain the contents of a suction canister directly into a public sewage system and to disinfect and clean the suction canister for disposal in a "white bag" without requiring any further treatment. White bags can be disposed of as ordinary garbage whereas red bags must be treated as infectious material.

The waste treatment system 10 generally consists of a canister-cleaning chamber 12 for holding the suction canister to be treated and a reservoir chamber 14 fluidly connected to the canister-cleaning chamber 12. The reservoir chamber 14 is adapted to be raised and lowered relative to the canister-cleaning chamber 12 to permit cleaning fluids to flow to and from the canister cleaning-chamber 12. The reservoir chamber 14 is also fluidly connected to a water source 16, a sewage system 18 and a disinfectant source 20.

The canister-cleaning chamber 12 is a generally cylindrical shaped chamber adapted for receiving a suction canister 22 for sanitation. The suction canister 22 is placed into the canister-cleaning chamber through an opening.

The canister-cleaning chamber 12 includes a generally circular top side 28 and a generally circular bottom side 30. A flexible housing 32 encloses a hollowed spike 34. The flexible housing 32 is sealing engaged to the canister-cleaning chamber 12 via a spike opening disposed in the bottom side 30 of the canister-cleaning chamber 12. In a preferred embodiment, a hand bar 36 is provided that can pivot. The hand bar 36 is operably connected to the hollowed spike 34 such that pivoting downward on the hand bar 36 causes the hollowed spike 34 to move in an upward direction and enter into the canister-cleaning chamber 12 via the spike opening. Pivoting downward on the hand bar 36 also breaks a release port disposed on the bottom of the suction canister 22. As described below, the suction canisters are specifically designed such that when the hollow spike 34 exerts sufficient force against the release port, the release port is broken and a drainage opening is created on the bottom of the suction canister 22. The drainage opening permits the body fluids to drain out of the suction canister 22 into the reservoir chamber 14 via a drainage tubing 40. The drained body fluids can then be further treated prior to disposal.

In a preferred embodiment, a showerhead 42 is disposed through the top side 28 of the canister-cleaning chamber 12 into the interior of the canister-cleaning chamber 12. The shower head 42 is preferably connected to a hot water source where the temperature of the hot water may for example, range from approximately 120 degrees Fahrenheit to approximately 140 degree Fahrenheit (49–60° C.).

The reservoir chamber 14 is slidably connected to a pole 46 so that the position of the reservoir chamber 14 relatively to the canister-cleaning chamber 12 may be adjusted. Adjustment of the position of the reservoir chamber 14 provides for manipulation the flow of fluids between the reservoir chamber 14 and the canister-cleaning chamber 12. In a preferred embodiment, an exhaust fan 26 is provided for exhausting fumes generated by the antiseptic. In a preferred embodiment, a controller may be employed to control the relative position of the reservoir chamber 14 to the canister-cleaning chamber 12 during the various stages of the suction canister sanitation process. The controller may be, for example, a microprocessor.

While a number of mechanisms may be employed to raise and lower the reservoir chamber 14 along the pole 46, in a preferred embodiment of the invention, hydraulics may be used.

The reservoir chamber 14 is preferably connected to a water source 16 where the temperature of the water provided is approximately 60 degrees Fahrenheit. The water is channeled from the water source 16 to the reservoir chamber 14 via water supply tubing 48. The disinfectant source 20 channels disinfectant to the reservoir chamber 14 via disinfectant supply tubing 50. Any type of disinfectant may be employed such as, for example, common household bleach or sodium hyperchlorite. In a preferred embodiment of the invention, a siphoning tube 52 is used to siphon the contents of the reservoir chamber 14 into the sewage system 18.

Referring now to FIGS. 1 through 4, the operation of the waste treatment system for suction canisters 10 is described. As shown in FIG. 1, when the waste treatment system for suction canisters 10 is first turned on, the controller initializes the system whereby the reservoir chamber 14 is lowered relative to the canister-cleaning chamber 12. In a preferred embodiment, a green indicator light 54 is employed to indicate to the user that the controller has placed the waste treatment system for suction canisters 10 in an initialization position. A suction canister 22 containing bodily fluids (V2) is placed within the canister-cleaning chamber 12 and locked into position.

Once the suction canister 22 has been secured within the canister-cleaning chamber 12, the user turns on an operating switch 57 to begin the sanitation process. In a preferred embodiment of the invention, upon recognizing that the operating switch 57 has been activated, the controller turns off the green indicator light 54 and turns on a red indicator light 56 to indicate that the waste treatment system for suction canisters 10 is in the sanitation cycle. The controller then issues two commands: one command releases a predefined volume of disinfectant from the disinfectant source 20 while the second command releases a predefined volume of water from the water source 16 into the reservoir chamber 14.

The predefined volume (V1) of disinfectant and water combined in the reservoir chamber 14 is designed to create an antiseptic solution having an optimum concentration for sanitizing both the suction canister 22 and the contents of the suction canister. In a preferred embodiment, an exhaust system may be employed to exhaust the aspirate generated by the disinfectant.

Figure 2:
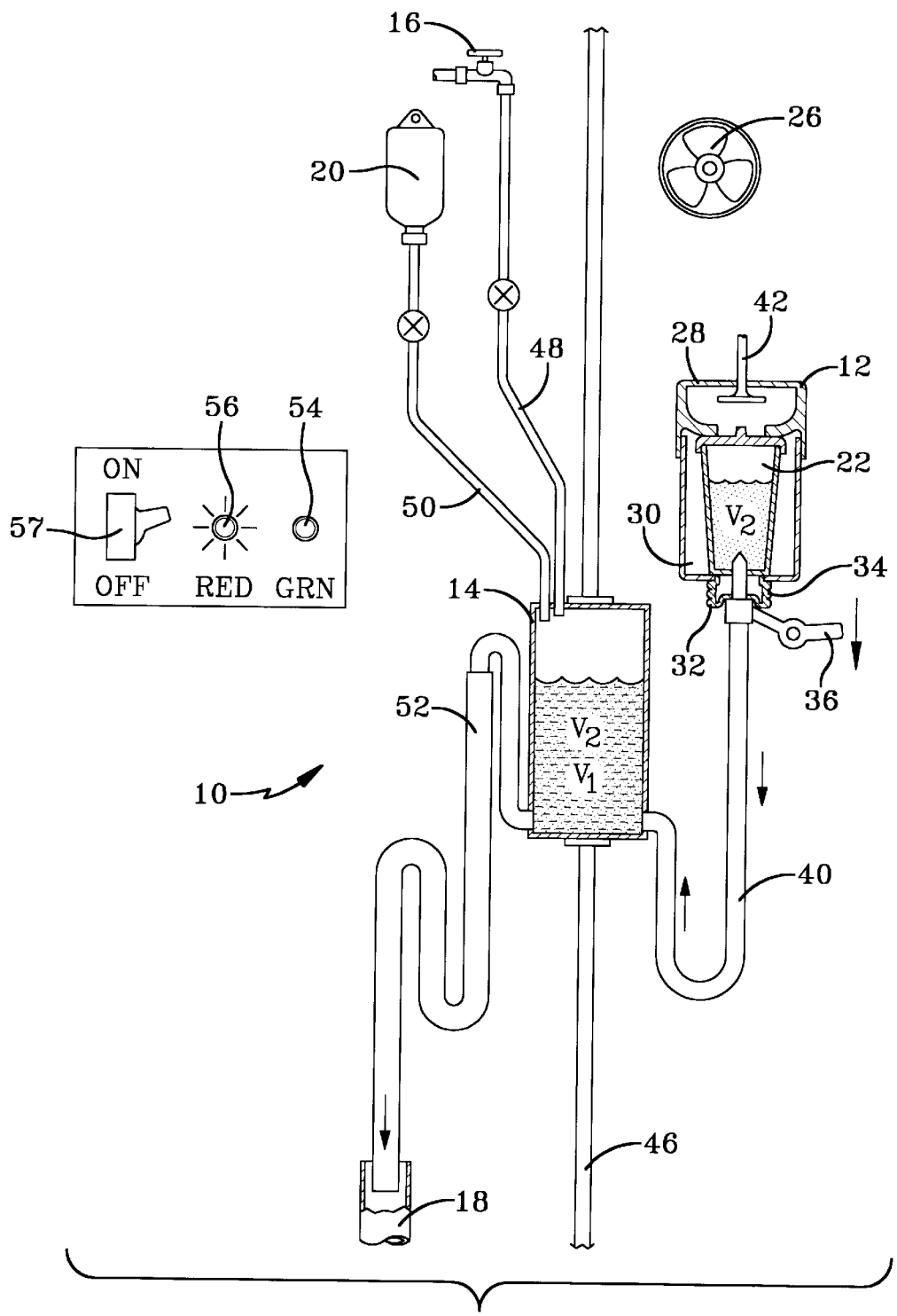
FIG. 2 is a front view in partial cross section of the waste treatment system for suction canisters of FIG. 1 illustrating the release of the fluid contents from the suction canister.

Referring now to FIG. 2, the releasing of the body fluid contents (V2) of the suction canister 22 is shown. The user pivots downward on the pivotal hand bar 36 which raises the hollow spike 34. When the hollow spike 34 exerts sufficient force against the release port, the release port is broken and a drainage opening is created on the bottom of the suction canister 22. Under the influence of gravity, the body fluids (V2) drain out of the suction canister 36 into the drainage tubing 40 which channels the fluids into the reservoir chamber 14 containing the antiseptic solution (V1). The body fluid (V2) is disinfected by the disinfectant diluted with water (V1). The controller allots a predefined period of time to permit the drainage of the body fluids (V2) from the suction canister 22 into the reservoir chamber 14.

Figure 3:
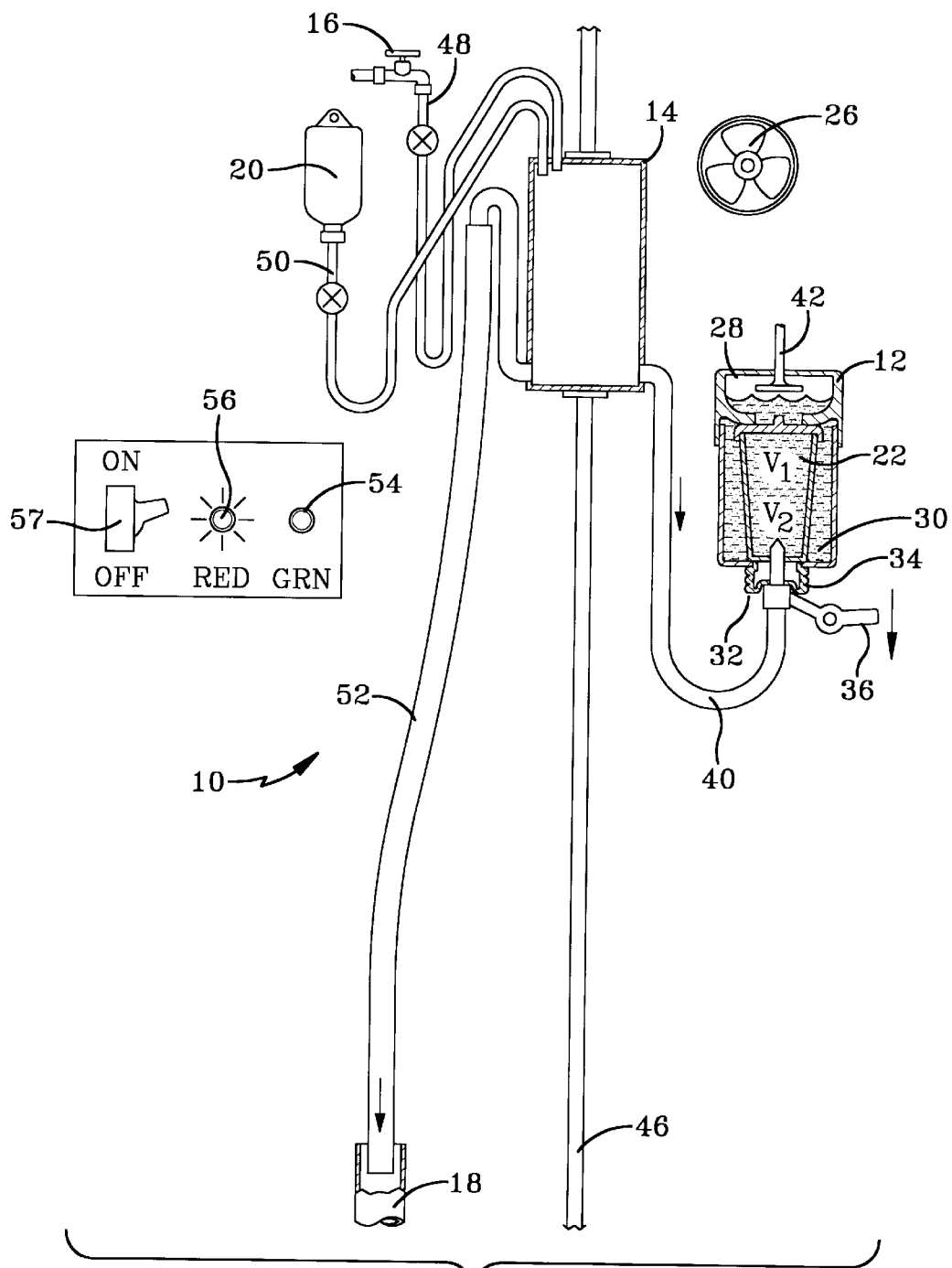
FIG. 3 is a front view in partial cross section of the waste treatment system for suction canisters of FIG. 1 illustrating the suction canister sanitation cycle.

Referring now to FIG. 3, the sanitizing of the suction canister 22 is shown. Once the predefined period of time for the drainage of the body fluids has passed, the controller issues a command to elevate the reservoir chamber 14 to a higher position relative to the canister-cleaning chamber 12. The influence of gravity caused by this elevation causes the mix of antiseptic solution and sanitized body fluids (V1+V2) to flow into the canister-cleaning chamber 12, soaking the entire canister 22. The controller maintains this position for a predefined incubation period to permit the antiseptic to sanitize the suction canister 22.

Figure 4:
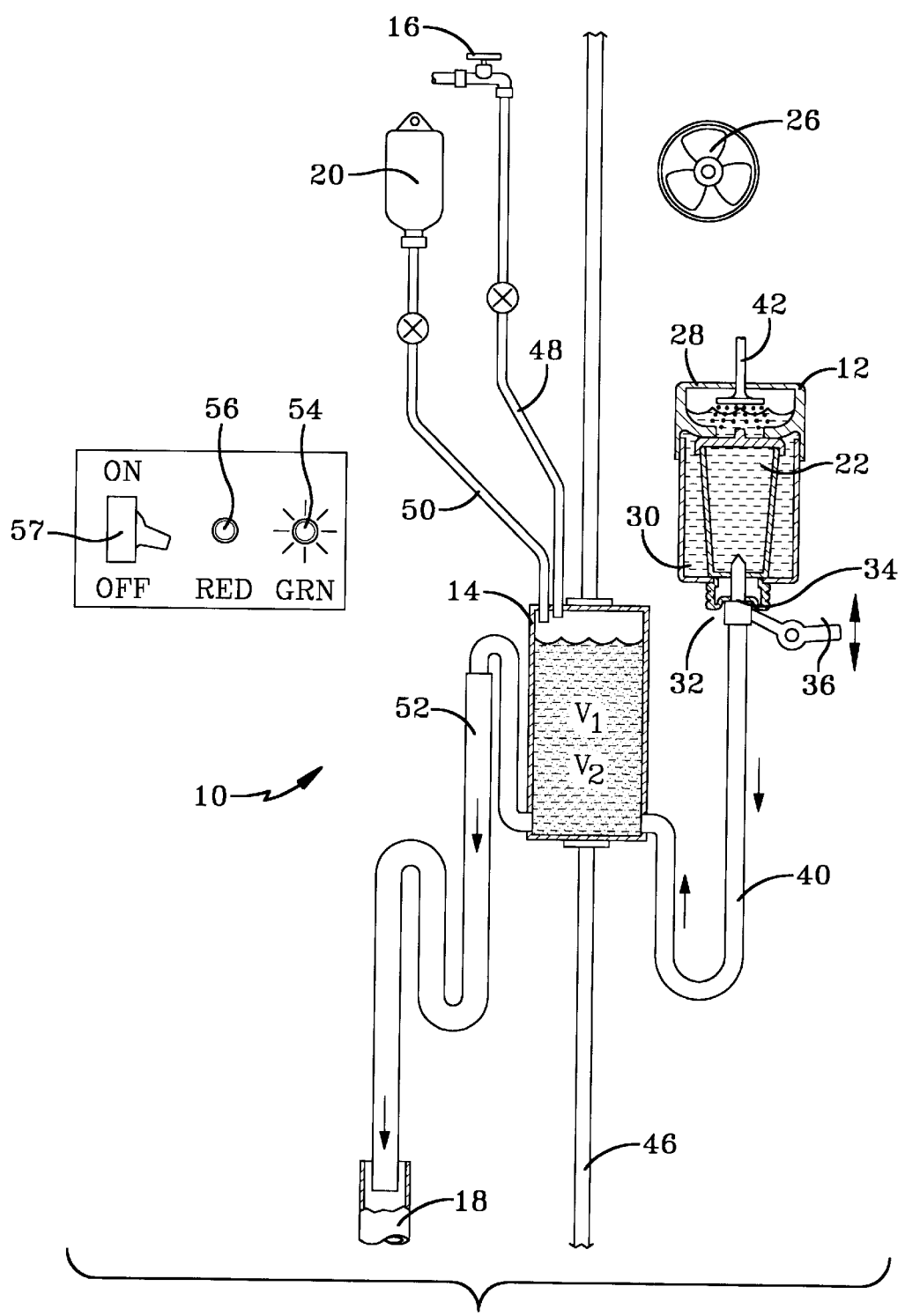
FIG. 4 is a front view in partial cross section of the waste treatment system for suction canisters of FIG. 1 illustrating the suction canister rinsing and waste fluid disposal cycle.

Referring now to FIG. 4, the rinsing and fluid disposal cycle is shown. Once the incubation cycle is complete, the controller issues a command to lower the reservoir chamber 14 relative to the canister cleaning chamber 12. The mix of antiseptic solution and sanitized body fluids (V1+V2) flow back into the reservoir chamber 14 via the drainage tubing 40. The mix of antiseptic solution and sanitized body fluids (V1+V2) then drains from the reservoir chamber 14 through the siphon tube 52 to the sewer 18.

The controller then issues a command to initiate the flow of water from the hot water source through the showerhead 42 into the canister-cleaning chamber 12. The hot shower water rinses the interior of the canister-cleaning chamber 12 and the exterior of the suction canister 22. Under the influence of gravity, the hot shower water is channeled into the reservoir chamber 14 via the drainage tubing 40. Again, the siphon acts to drain the liquids collected into the reservoir chamber 14 into the sewage drain 18 via the siphon tubing 52. Once the reservoir chamber 14 has been drained of all waste fluids, the controller issues a command to turn on the green indicator light 54 and the red indicator light 56 is turned off. The user can then withdraw the sanitized suction canister 22 from the system and discard the suction canister 22 into a "white bag" for disposal.

While the preferred embodiment of the invention discloses a specific sequence for the flow of antiseptic fluids and body fluids between the reservoir chamber 14 and the canister-cleaning chamber 12 to facilitate the sanitation of the suction canister 22, alternative sequences and flow manipulations employing the principles of gravitational flow and siphonic flow to achieve sanitation and disinfection of the suction canister 22 and its contents are considered to be within the scope of the invention.

Figure 5:
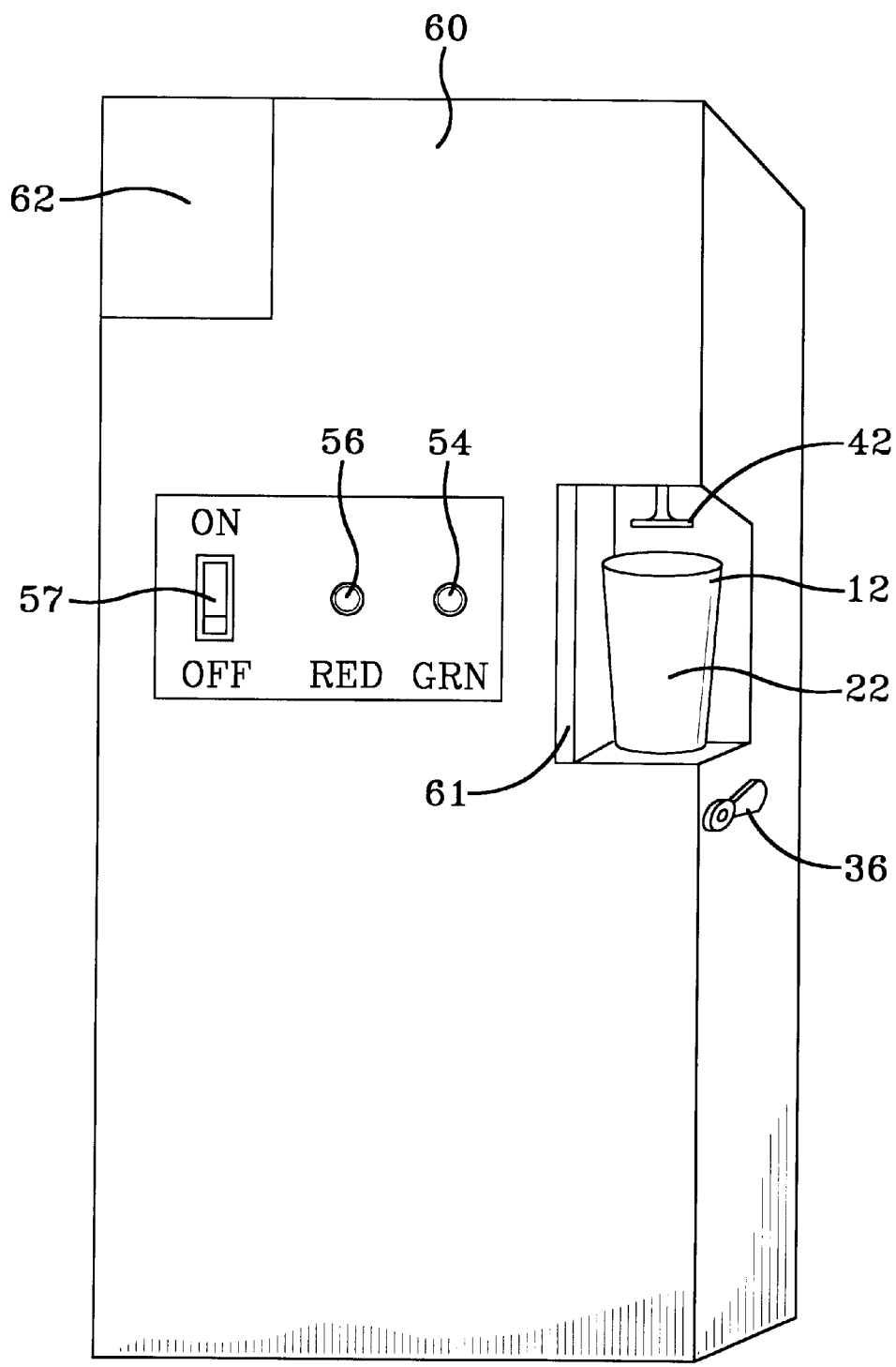
FIG. 5 is a perspective view of one embodiment of a cabinet for housing the waste treatment system for suction canisters in accordance with the principles of the present invention.

Referring now to FIG. 5, an example of a cabinet 60 for housing the waste treatment system for suction canisters is shown. The cabinet includes a sliding door 61 to close the opening in the canister-cleaning chamber 12 to gain access to the suction canister 22. The user can open the sliding door 61 to place the suction canister 22 in the system. The sliding door 61 is secured to seal the canister-cleaning chamber 12. The seal minimizes the likelihood that cleaning personnel will be exposed to the aerosol created during the draining and sanitation of the suction canister 22. The user can open the sliding door to withdraw the sanitized suction canister 22 from the system.

The cabinet 60 includes a reload door 62 providing access to the disinfectant source 20. The cabinet also includes a switch 57 for turning on the system, the green indicator light 54 and the red indicator light 56 on the front surface of the cabinet 60.

While the preferred embodiment of the cabinet for housing the waste treatment system for suction canisters and the preferred placement of doors, switches and lights are shown, other forms of cabinets or housing and alternative placements of doors, switches and lights may be used without departing from the spirit of the invention. Alternative embodiments where the waste treatment center for suction canisters is modified to accommodate the sanitation of multiple suction canisters are also considered to be within the scope of the invention.

Figure 6:
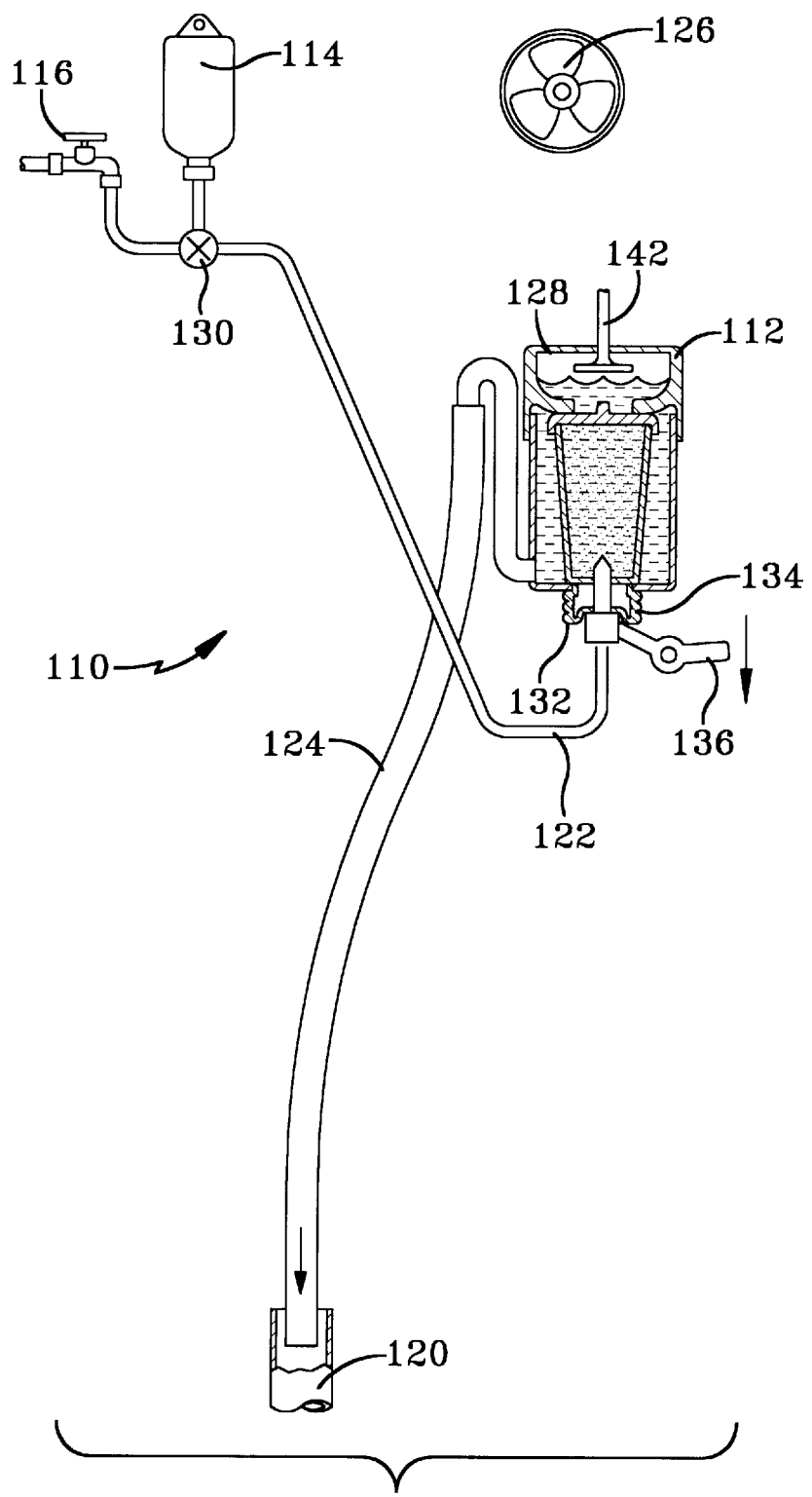
FIG. 6 is a front view of an alternative embodiment of a waste treatment system for suction canisters in accordance with the principles of the present invention.

Referring now to FIG. 6, an alternative embodiment of a waste treatment system for suction canisters in accordance with the principles of the present invention is designated generally by 110. This alternative embodiment of the waste treatment system for suction canisters 110 generally includes a canister-cleaning chamber 112, an antiseptic source 114, a warm water source 116, a hot water source and a sewage drain 120. Supply tubing 122 is used to fluidly connect the antiseptic source 114 and the warm water source 116 to the canister-cleaning chamber 112. Drainage tubing 124 is used to provide fluid connection from the canister-cleaning chamber 112 to the sewage drain 120. In a preferred embodiment, an exhaust fan 126 is provided for exhausting fumes generated by the antiseptic. A controller is used to control the operation of the waste treatment system.

In operation, a suction canister 128 containing body fluids is positioned and secured within the canister-cleaning chamber 112. The controller issues two commands: one command releases a predefined volume of antiseptic from the antiseptic source 114 while the second command releases a predefined volume of water from the warm water source 116. In a preferred embodiment, a mixer 130 is used to mix the antiseptic with the warm water to obtain a predefined dilution factor for the antiseptic solution.

A hollowed spike 132 is used to break the release port disposed on the bottom side of the suction canister 128. A flexible housing 132 encloses a hollowed spike 134. In a preferred embodiment, a hand bar 136 is provided that can pivot. Gravity forces the antiseptic solution to flow into the canister-cleaning chamber 112 and soak both the suction canister 128 and its contents. Following an incubation period sufficient to disinfect both the suction canister 128 and its contents, hot water is introduced into the canister-cleaning chamber 112 via a showerhead 142. The hot water is used to rinse the interior of the canister-cleaning chamber 112 and the exterior of the suction canister 128. As the liquid level rises within the canister-cleaning chamber 112, siphon action causes the liquid to be siphoned out via the drainage tubing 124 into the sewage drain 120. Once the liquid within the canister-cleaning chamber 112 has been drained, the suction canister 128 can be removed for "white bag" disposal.

While the invention has been described with specific embodiments, other alternatives, modifications and variations will be apparent to those skilled in the art. Accordingly, it is intended to include all such alternatives, modifications and variations set forth within the spirit and scope of the appended claims.

What is claimed is:

1. A waste treatment system for suction canisters comprising:
   a canister-cleaning chamber for holding the suction canister to be treated;
   a reservoir chamber fluidly connected to the canister-cleaning chamber and to a water source, the reservoir chamber adapted to be raised and lowered relative to the canister-cleaning chamber to permit cleaning fluids to flow to and from the canister-cleaning chamber; and
   means to permit drainage of body fluids from the suction canister.

2. The waste treatment system for suction canisters of claim 1, further wherein the reservoir chamber is fluidly connected to a sewage system.

3. The waste treatment system for suction canisters of claim 1, further including a hand bar connected to a hollowed spike, whereby pivoting downward on the hand bar causes the hollowed spike to enter into the canister-cleaning chamber.

4. The waste treatment system for suction canisters of claim 1, further including a hand bar, whereby pivoting downward on the hand bar breaks a release port disposed on the suction canister.

5. The waste treatment system for suction canisters of claim 1, further including a controller to control the relative position of the reservoir chamber to the canister-cleaning chamber.

6. The waste treatment system for suction canisters of claim 5, further wherein the controller is a microprocessor.

7. The waste treatment system for suction canisters of claim 1, further including a shower head disposed in the canister-cleaning chamber.

8. The waste treatment system for suction canisters of claim 1, further wherein the reservoir chamber is fluidly connected to a disinfectant source.

* * * * *